United States Patent
Venchiarutti et al.

[11] Patent Number: 6,142,019
[45] Date of Patent: Nov. 7, 2000

[54] METHOD OF DETERMINING SURFACE ACOUSTIC WAVE PATHS

[75] Inventors: Barbara Venchiarutti, Schenectady; Peter William Lorraine, Niskayuna; Robert John Filkins, Fonda, all of N.Y.

[73] Assignee: General Electric Co., Schenectady, N.Y.

[21] Appl. No.: 09/235,915

[22] Filed: Jan. 25, 1999

Related U.S. Application Data

[60] Provisional application No. 60/091,020, Jun. 29, 1998.

[51] Int. Cl.⁷ ................................................. G01N 29/22
[52] U.S. Cl. ................................................. 73/602
[58] Field of Search ........................ 73/602; 702/39, 702/40, 56, 6

[56] References Cited

U.S. PATENT DOCUMENTS

| | | | |
|---|---|---|---|
| 4,241,610 | 12/1980 | Anderson | 73/626 |
| 4,503,708 | 3/1985 | Kimo et al. | 73/628 |
| 5,456,114 | 10/1995 | Liu et al. | 73/597 |
| 5,760,904 | 6/1998 | Lorraine et al. | 356/360 |
| 5,765,408 | 6/1998 | Lindgren et al. | 73/597 |
| 5,801,312 | 9/1998 | Lorraine et al. | 73/602 |
| 5,854,450 | 12/1998 | Kent | 178/18.04 |
| 5,894,092 | 4/1999 | Lindgren et al. | 73/598 |
| 5,963,447 | 10/1999 | Kohn et al. | 364/148.04 |

*Primary Examiner*—Hezron Williams
*Assistant Examiner*—Rose M. Miller

[57] ABSTRACT

A method for determining surface acoustic wave ray paths for an object. The method includes obtaining a representation of the object. A plurality of geodesics from a point on the object are determined and a plurality of surface acoustic wave ray paths are defined in response to the plurality of geodesics. The acoustic wave ray paths are used to determine a plurality of equally spaced surface acoustic wave fronts. In one application the surface acoustic wave fronts may then be used in a synthetic aperture focusing technique to obtain an image of the object.

15 Claims, 6 Drawing Sheets

6,142,019

METHOD OF DETERMINING SURFACE ACOUSTIC WAVE PATHS

CROSS-REFERENCE TO RELATED APPLICATIONS

This application claims the benefit of U.S. Provisional Application Ser. No. 60/091,020 filed Jun. 29, 1998.

BACKGROUND OF THE INVENTION

The invention relates to a method of computing surface acoustic wave ray paths on complex curved surfaces for use in laser applications such as ultrasound non-destructive evaluation (NDE). Laser ultrasonic imaging is used to generate high resolution images of an object and may be used to inspect a surface for defects. U.S. Pat. Nos. 5,760,904 and 5,801,312, assigned to the assignee of the present invention and incorporated herein by reference, disclose systems for imaging an object using laser ultrasound. Both of these patents disclose use of synthetic aperture focusing techniques (SAFT) to laser ultrasound generated surface waves for rapid wide-area imaging of surface and near surface defects from limited scan areas including single lines. The basic SAFT algorithm relies on what is referred to as the delay and sum method. In essence, it uses the ultrasound propagation delays between the source and image points over the inspected surface or volume.

The success of the SAFT is tied to knowing the surface acoustic wave (SAW) ray paths and wave fronts on the surfaces. On simple, Euclidean surfaces (e.g. flat surfaces) such paths can be easily defined by assuming a point source of sound in the far field and observing that the rays essentially trace out meridians or radii from the point source. For more complex surfaces, there is a need in the art for a method of tracing SAW ray paths and wave fronts on the surface to allow for laser ultrasound inspection of such complex surfaces.

BRIEF SUMMARY OF THE INVENTION

An exemplary embodiment of the invention is directed to a method for determining surface acoustic wave ray paths for an object. The method includes obtaining a representation of the object. A plurality of geodesics from a point on the object are determined and a plurality of surface acoustic wave ray paths are defined in response to the plurality of geodesics. The acoustic wave ray paths are used to determine a plurality of equally spaced surface acoustic wave fronts. In one application the surface acoustic wave fronts may then be used in a synthetic aperture focusing technique to obtain an image of the object.

BRIEF DESCRIPTION OF THE DRAWINGS

Referring now to the drawings wherein like elements are numbered alike in the several Figures.

DETAILED DESCRIPTION OF THE INVENTION

Figure 1:
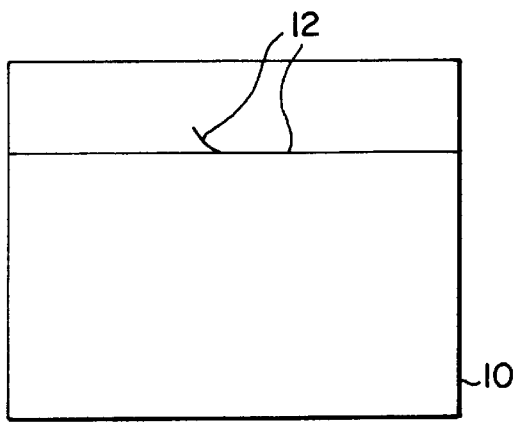
FIG. 1 illustrates a surface having defects.
Figure 2:
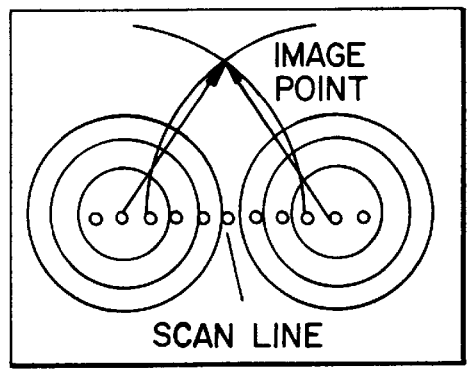
FIG. 2 depicts scanning of the surface of FIG. 1 with laser ultrasound waves.
Figure 3:
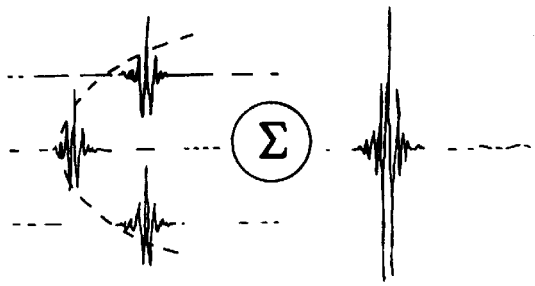
FIG. 3 depicts the process of summing signals detected in the scanning process.

FIGS. 1–3 illustrate the process of inspecting a planar part using laser ultrasound scanning. FIG. 1 illustrates a planar part 10 to be inspected for defects. The part 10 includes cracks 12. FIG. 2 illustrates the scanning of the part 10 using a laser ultrasound inspection system such as that disclosed in U.S. Pat. Nos. 5,760,904 and 5,801,312. The laser ultrasound inspection system includes a laser beam source and a laser probe beam measured with an interferometer. The source, for example a focused ring of light, excites the surface and produces ultrasound waves by thermoelastic expansion. The waves generated by the source propagate outwards and scatter off flaws (or other material disturbances). The scattered sound waves are measured by the laser probe beam. As the surface is scanned, a series of position-time records are gathered at each position of the transducer. The synthetic aperture algorithm combines these records to produce an image by mapping the measured waveforms onto the equidistant loci of the sound field and summing the results as shown in FIG. 3.

Figure 4:
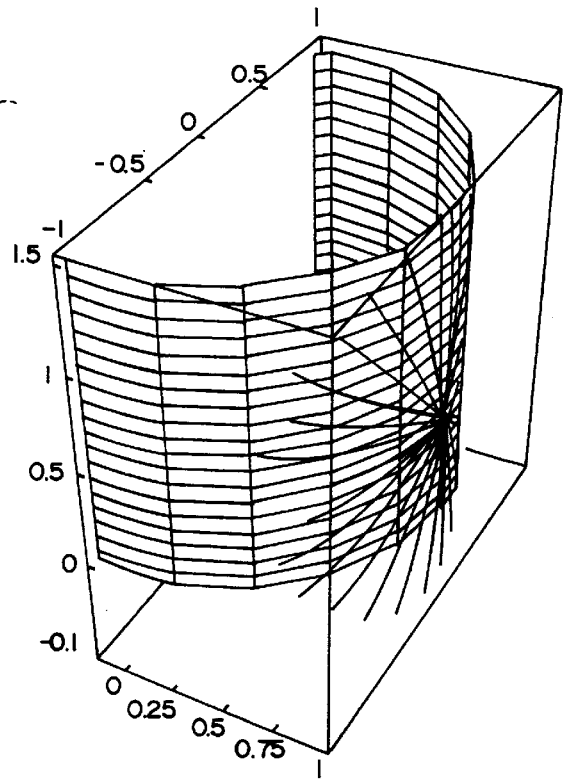
FIG. 4 is a perspective view of a cylinder and geodesics for a point of the cylinder.
Figure 5:
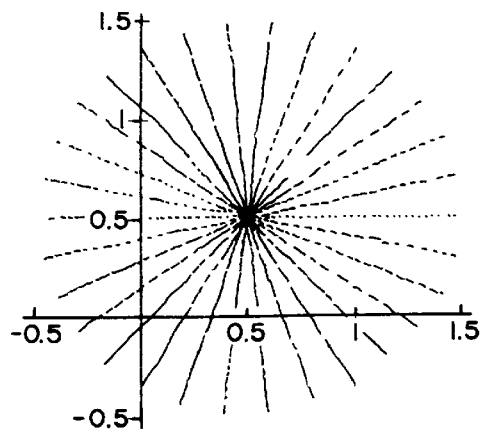
FIG. 5 is a projection on a plane of the geodesics of FIG. 4.
Figure 6:
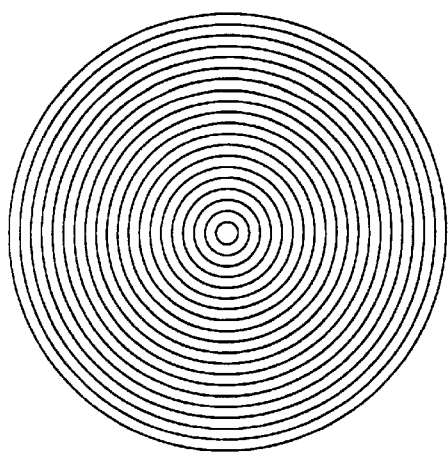
FIG. 6 is a projection on a plane of equally spaced wave fronts for the cylinder of FIG. 4.

If the surface has a planar shape, the equidistant field will consist of concentric circles and mapping the measured waveforms onto the equidistant loci of the SAW wave fronts is based on simple, circular geometry. More complex surfaces produce SAW wave fronts having complex shapes. FIGS. 4–9 illustrate the differing wave fronts for two geometries. FIG. 4 is a perspective view of a cylinder with geodesics for a point on the surface of the cylinder shown superimposed on the cylinder. FIG. 5 is a projection on a plane of the cylinder geodesics and FIG. 6 is a projection on a plane of equally spaced wave fronts for the cylinder. As shown in FIG. 6, the SAW wave fronts are represented by a series of concentric circles.

Figure 7:
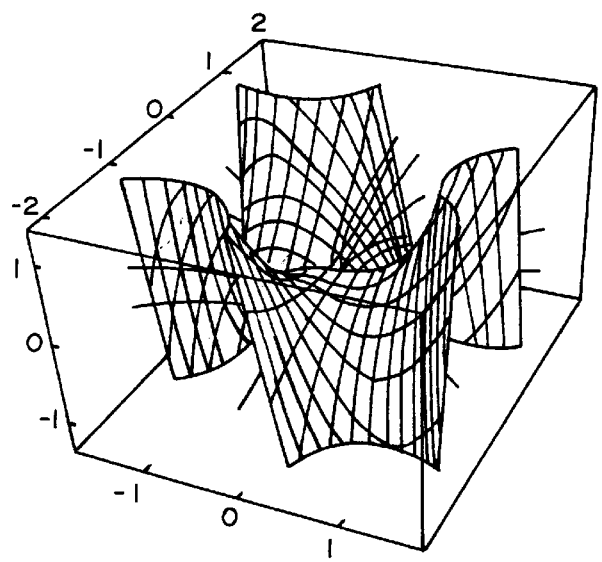
FIG. 7 is a perspective view of a monkeysaddle and geodesics for a point on the monkeysaddle.
Figure 8:
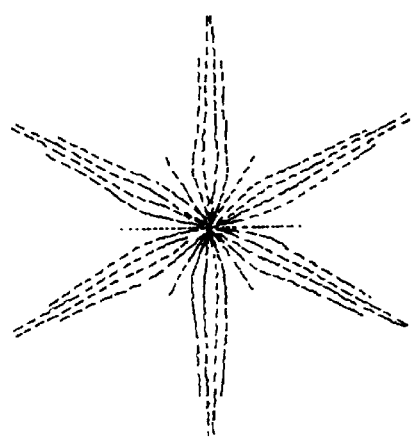
FIG. 8 is a projection on a plane of the geodesics of FIG. 7.
Figure 9:
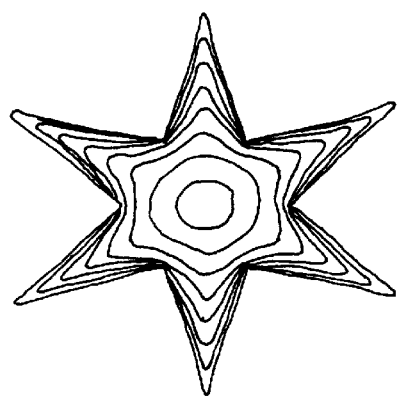
FIG. 9 is a projection on a plane of equally spaced wave fronts for the monkeysaddle of FIG. 7.

FIG. 7 is a perspective view of a monkeysaddle with geodesics for a point on the monkeysaddle shown superimposed on the monkeysaddle. FIG. 8 is a projection on a plane of the monkeysaddle geodesics and FIG. 9 is a projection on a plane of equally spaced wave fronts for the monkeysaddle. As is clear from FIG. 9, the more complex the surface, the more complex the loci of equidistant SAW wave fronts. Since the SAFT reconstruction process maps the measured values to points on the loci of equidistant wave fronts, it is necessary to know the SAW ray paths and SAW wave fronts for any surface.

Figure 10:
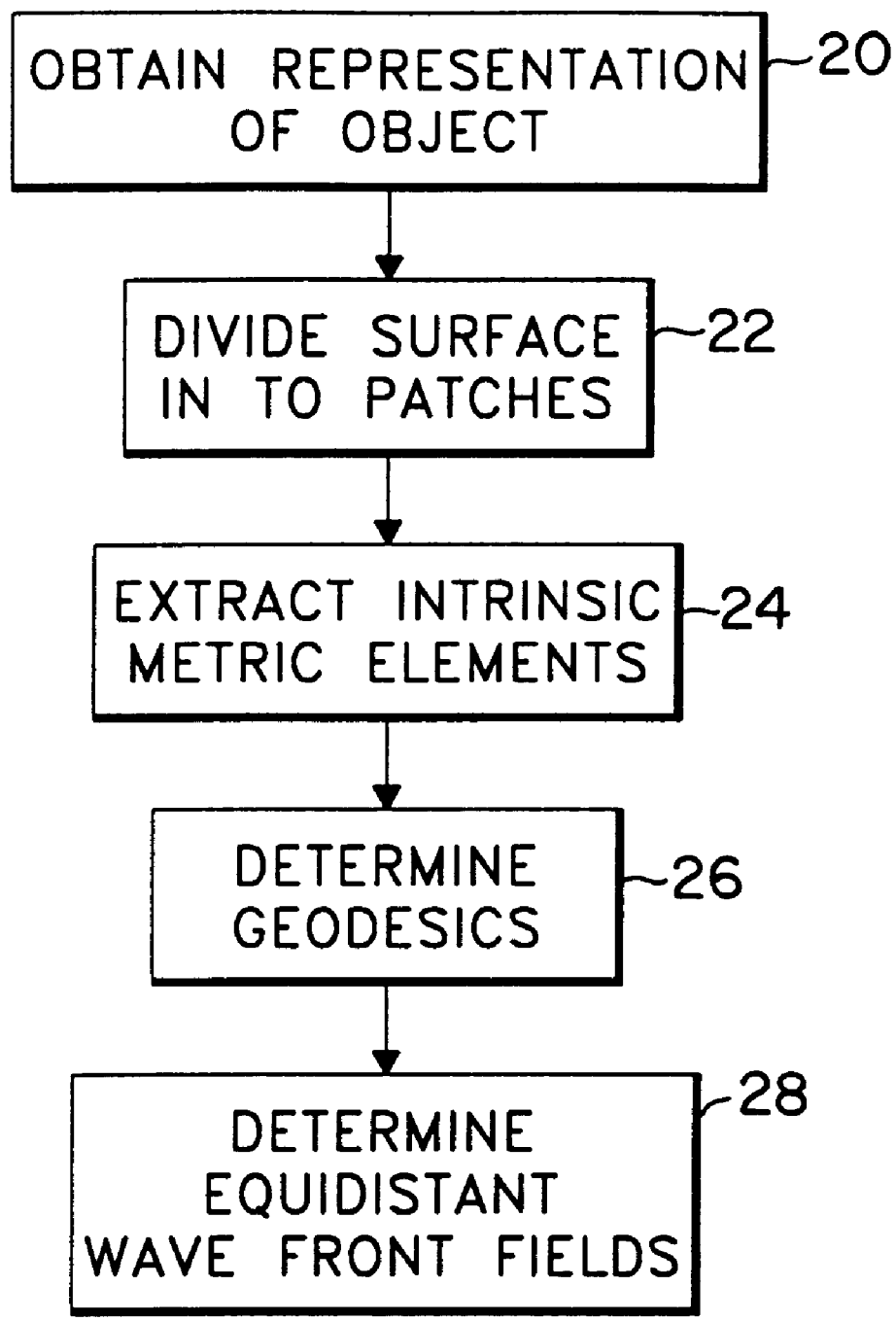
FIG. 10 is a flowchart of a process of determining SAW wave fronts in an exemplary embodiment of the invention.

An exemplary embodiment of the invention is a method for determining all possible SAW ray paths and wave front positions from any given point on the surface. FIG. 10 is a flowchart of the process of determining the SAW ray paths and wave fronts. At step 20, the shape of the object to be processed is obtained. This may be performed empirically by direct measurement with a metrology device or obtained from a preexisting source such as a CAD file. At step 22, the surface is represented by a series of patches that have parametrical expression obtained by the Non Uniform Rational B-Spline fitting technique described herein. The parametrical expression is then used to extract the intrinsic metric elements, in particular the Christoffel symbols, required for the solution of the geodesic equations at step 24. At step 26 the geodesic equations are solved to provide the geodesics for the surface which, as described in more detail below, correspond to the SAW ray paths. The geodesics correspond to the ray paths along the patches of the surface, and the starting point of the ray propagation corresponds to the boundary condition of the geodesic equations. Once these geodesics are calculated, the extrapolation and the plot of all the coordinates at the same distance from the center of propagation, gives the equidistant field, or the wave front field as shown at step 28. As described above, the equidistant wave front field may then be used in the SAFT reconstruction of the surface waves.

The representation of the surface by a series of patches at step 22 involves a Non-Uniform Rational Bicubic Spline (NURBS) interpolation. The NURBS technique has been implemented to reproduce complex engine part surfaces with the maximum of fidelity. Since complex surfaces cannot be simply fit, the surfaces are represented by a series of overlapping patches or regions. These patches, which become the building blocks to approximate the whole surface, are bivariate parametric polynomials of the 3rd order. The goal is to insure continuity within each patch as well as across patch boundaries in order to accurately reproduce the acoustic ray paths. The $C^2$ continuity is assured by the NURBS technique. The parametric expressions of the fitted patches are obtained by linear combinations of basis functions with appropriate coefficients, that are referred to as control points. The number of control points depends on the number of patches used for the fitting. The two independent parameters that characterize the surface over a certain range, are divided into monotone sequences of intervals or knot segments. Over each interval of the two independent parameters, third order polynomials, which are sets of basis functions, are defined and are matched in values and derivatives at their junctures. For the evaluation of the B-Spline basis, the computational procedure developed by Cox and DeBoor, shown below, is used.

COX-DE BOOR ALGORITHM

The case of a curve spline fitting is shown below
n=degree of the spline
m=n+1 order of the spline
N=number of control points
M=N+m number of knot points
Parameter range division
Knot sequence: $(u_1, u_2, \ldots, u_{N+m})$ $u_{j+1} \geq u_j$
Cox-De Boor Algorithm
$B_{i,1}(u) = 1$ $u_i \leq u < u_{i+1}$
$B_{i,1}(u) = 0$ otherwise $$B_{i,m}(u) = \frac{u - u_i}{u_{i+m-1} - u_i} B_{i,m-1} + \frac{u_{i+m} - u}{u_{i+m} - u_{i+1}} B_{i+1,m-1} \quad u_i \leq u < u_{i+1}$$

A degree n spline function for a parametrized curve has this form $$\chi(u) = \Sigma_{i=1 \ldots N} a_i B_{i,m}(u)$$

where the coefficients $a_i$ are the control points. The surface interpolation representation is an application of a tensor product spline and has the form $$S(u,v) = \Sigma_{i=1 \ldots N1} \Sigma_{j=1 \ldots N2} a_{ij} B_{i,m}(u) B^-_{j,m}(v).$$

The linear combinations of the polynomial basis function sets with the control points at each knot interval, give the parametric expressions for the patches. From these expressions, the intrinsic geometric properties of the surface are derived and the geodesic curves along the inspected part may be calculated as described below.

At step 26 in FIG. 10, the process determines the geodesics for the surface which are equated to the SAW ray paths over the surface. The equivalence between a geodesic on a curved surface and acoustic ray paths is described herein. As with the well known laws of geometric optics, light rays are null geodesics. Since the wave equations governing the propagation of light waves and sound are basically the same, it follows that in the high frequency limit (that of ultrasound), it can be asserted that ultrasound rays will also be null geodesics. This basic concept is related to Einstein's equivalence principle. It therefore follows that the problem of tracing ultrasound rays emanating from a disturbance on the surface of object being evaluated by SAFT is reduced to solving for the null geodesics in the curved space created by the surface of the test object. The equivalence between geodesics and ultrasound ray paths is demonstrated below.

The parametric expressions of the patches, as a representation of the real part, are useful to obtain the intrinsic geometric properties for the determination of the geodesics. The information extracted from the patch expressions is common in the field of differential geometry. These concepts are the first form of the intrinsic metric and the Christoffel symbols.

In general, an n-dimensional patch is an n-dimensional set of differentiable functions depending on the two parameters (u, v) that define the local surface $$x(u,v) = (x^1(u,v), \ldots, x^\lambda(u,v), \ldots, x^n(u,v))$$

The partial derivatives of x(u, v) help to define the local tangents $$x_u = \frac{\partial x(u, v)}{\partial u} = \left( \frac{\partial x^1(u, v)}{\partial u}, \ldots, \frac{\partial x^\lambda(u, v)}{\partial u}, \ldots, \frac{\partial x^n(u, v)}{\partial u} \right)$$

$$x_v = \frac{\partial x(u, v)}{\partial v} = \left( \frac{\partial x^1(u, v)}{\partial v}, \ldots, \frac{\partial x^\lambda(u, v)}{\partial v}, \ldots, \frac{\partial x^n(u, v)}{\partial v} \right)$$

The intrinsic metric or Riemannian metric is a symmetric tensor $g_{uv}$ that defines the infinitesimal distance ds between two nearby events or points in multidimensional curved or flat spaces.

$$ds^2 = \sum_{uv=0}^{n} g_{uv} dx_u dx_v$$

For the patch x(u, v) the Riemannian representation immediately reduces to the first fundamental form based on the surface coordinates u, v $$ds^2 = E\, du^2 + F\, du\, dv + G\, dv^2$$

with $E = \|x_u\|$, $F = x_u \cdot x_v$, $G = \|x_v\|$ and are essentially the basis set along the surface.

The Christoffel Symbols are symmetric objects that help define the free trajectories of particles in curved spaces. They obey non linear transformation rules between different coordinate systems in inertial frames. They depend on the metric tensor coefficients and relative partial derivatives. The Christoffel symbols can be defined in terms of the intrinsic metric as follows:

$$\Gamma_{ij}^k = \sum_{k=1}^{n} \left(\frac{1}{2}\right) g^{lk}(g_{il,j} + g_{lj,i} - g_{ji,l})$$

$$g_{il,j} = \frac{\partial g_{il}}{\partial x_j}$$

Along the surface, the definition of the Christoffel symbols in terms of the basis set of the surface are $$\Gamma_{uu}^u = \frac{GE_u - 2FF_u + FE_v}{2(EG - F^2)} \quad \Gamma_{uu}^v = \frac{2EF_u - EE_u + FE_u}{2(EG - F^2)}$$

$$\Gamma_{uv}^u = \frac{GE_u - FG_u}{2(EG - F^2)} \quad \Gamma_{uv}^v = \frac{EG_u - FE_v}{2(EG - F^2)}$$

$$\Gamma_{vv}^u = \frac{2GF_v - GG_u + FG_v}{2(EG - F^2)} \quad \Gamma_{vv}^v = \frac{EG_v - FF_v + FG_u}{2(EG - F^2)}$$

A geodesic curve is the parametric solution (the parameter is the length t of the curves) of the governing geodesic equation, which is a differential equation of the second order with coefficients represented by the Christoffel symbols. The general form of the governing geodesic equation is $$\frac{d^2 x^\lambda(t)}{dt^2} + \Gamma_{\mu\nu}^\lambda \frac{dx^\mu(t)}{dt} \frac{dx^\nu(t)}{dt} = 0$$

For the problem under consideration, the governing set of geodesic equations for one curve reduce to $$\frac{d^2 u(t)}{dt^2} + \Gamma_{uu}^u \frac{du(t)^2}{dt} + \Gamma_{uv}^u \frac{du(t)}{dt}\frac{dv(t)}{dt} + \Gamma_{vv}^u \frac{dv(t)^2}{dt} = 0$$

$$\frac{d^2 v(t)}{dt^2} + \Gamma_{uu}^v \frac{dv(t)^2}{dt} + \Gamma_{uv}^v \frac{du(t)}{dt}\frac{dv(t)}{dt} + \Gamma_{vv}^v \frac{dv(t)^2}{dt} = 0$$

with the applicable boundary conditions.

In order to have exact solutions for the physical surface of interest, the equation requires four boundary conditions. For each geodesic calculated in the first patch, the boundary conditions are the values of the coordinates of the center point of the patch and their derivatives with respect to the parameter t. It follows that the geodesic equations evaluated on the adjoining patches have different coefficients and different boundary conditions. The coefficients are the Christoffel symbols of the metric of the other patches. The boundary conditions become the intersection points of the previous geodesics with the borders and their respective first derivatives. This leads to 2n boundary conditions for the n-dimensional patch case $$x^\lambda(t = 0) = c, \left.\frac{dx^\lambda(t)}{dt}\right|_{t=0} = d$$

$$\lambda = 1, \cdots, n$$

and 4 boundary conditions for the case of interest $$u(t = 0) = c1, \left.\left|\frac{du(t)}{dt}\right|\right|_{t=0} = d1$$

$$v(t = 0) = c2, \left.\left|\frac{dv(t)}{dt}\right|\right|_{t=0} = d2$$

The equivalence of acoustic rays on isotropic surfaces and geodesics along the same surface is useful to the present invention. If an accurate representation of a complex surface and the geodesics of interest emanating from a given point (i.e. the SAFT SAW source) are defined, then the SAW ray paths and equidistant wave fronts are also defined. As described above, the location of the equidistant SAW ray wave fronts are used in applying SAFT reconstruction technique.

It is significant to compare the difference in both the equidistant wave fronts and the ray paths in the case of planar surfaces (FIGS. 4–6) and complex surfaces (FIGS. 7–9). For arbitrary curved shapes the ray paths are not straight lines, but instead curves that satisfy the geodesic equations related to non-Euclidean spaces. Without the use of differential geometry utilized by the invention, it would not be possible to calculate the correct ray paths.

Figure 11:
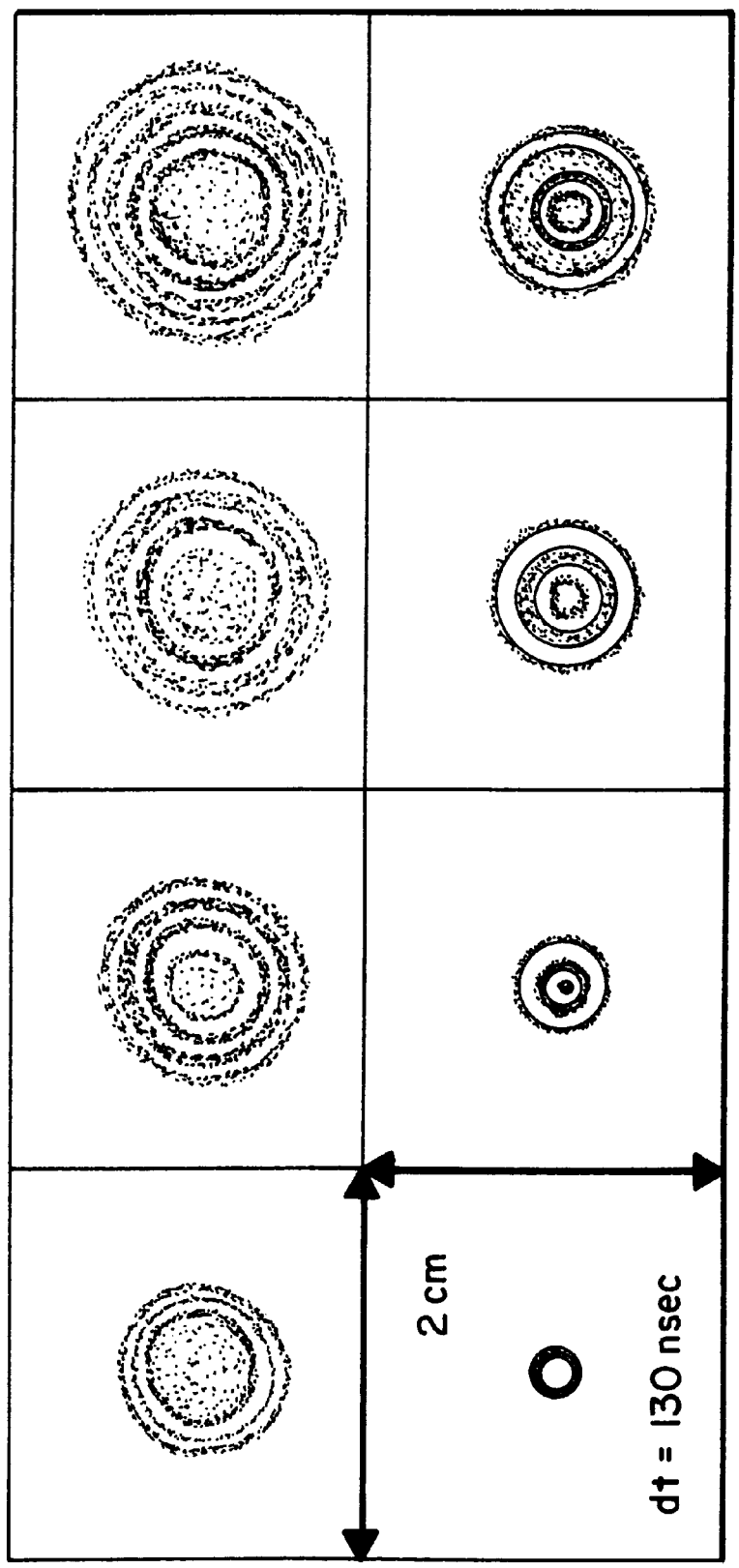
FIG. 11 illustrates a process of empirically measuring SAW wave fronts.

FIG. 11 depicts a method of measuring the SAW ray paths and equidistant wave fronts. A point on the object is selected as an origin and a laser interferometer is directed at the origin. A laser source is then scanned along scan lines on the object and ultrasonic signals are collected at the origin. A C-scan technique may be used to image the actual SAW wave fronts. The measured SAW wave fronts can the be compared to SAW wave fronts derived using the method shown in FIG. 10 to confirm that the object is accurately modeled by the method shown in FIG. 10. The measured SAW wave fronts may also be used directly to yield equidistant SAW wave fronts necessary for the SAFT reconstruction process.

An exemplary application of the invention will now be described. The present invention may be used to calculate an approximate representation of a seal from an aircraft engine. The invention determines the geometric information necessary to calculate the trajectories of ultrasound surface waves along the surface of the seal. An area on the seal which is relevant for the inspection is a 50 mm$^2$ portion. A sequence of nine patches approximates the modeled part with an error less then 0.8%. The dimensions of each patch are 12 mm×50 mm. Through use of the NURBS process described above, the geodesics calculated across the patches satisfy C$^2$ continuity at the borders.

Figure 12:
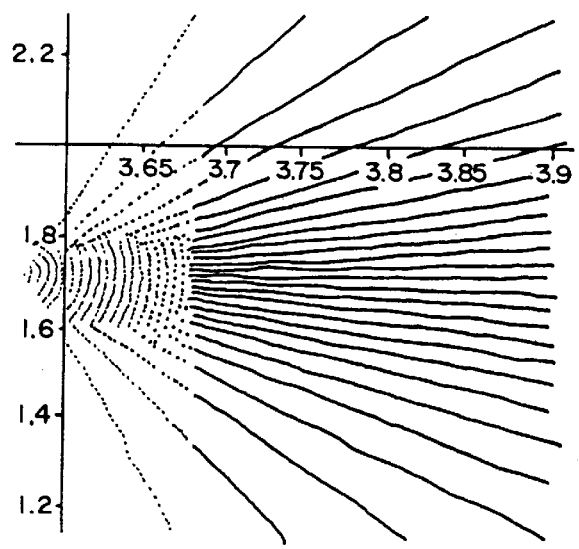
FIG. 12 illustrates geodesics for two adjacent patches.
Figure 13:
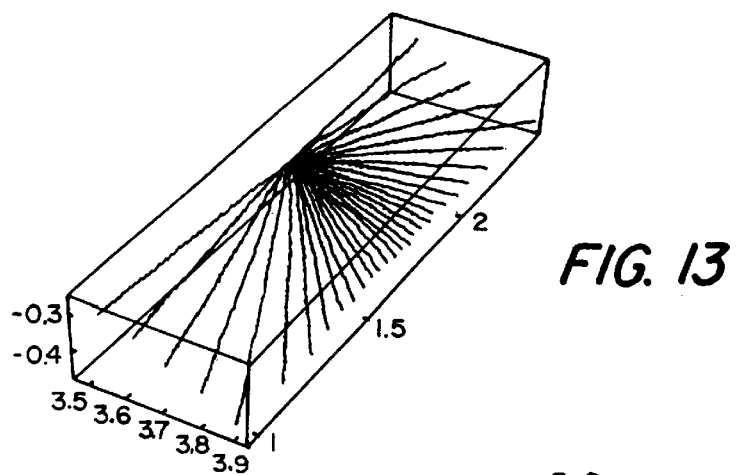
FIG. 13 is a perspective view of geodesics in three dimensions.
Figure 14:
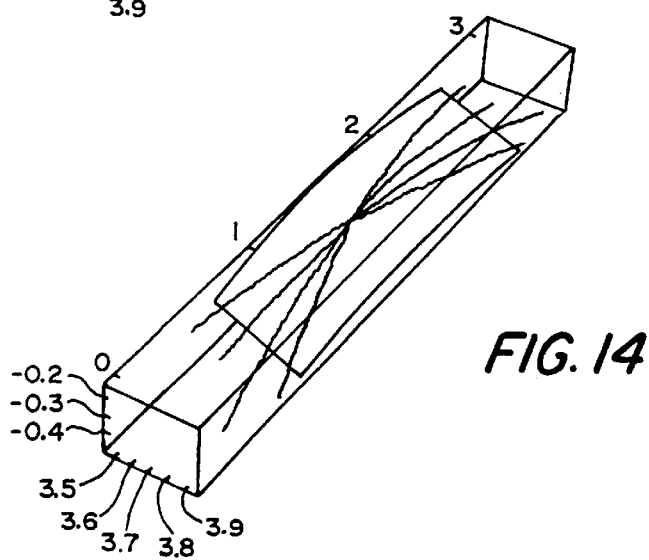
FIG. 14 is a perspective view of the geodesics of FIG. 12 superimposed on two patches.
Figure 15:
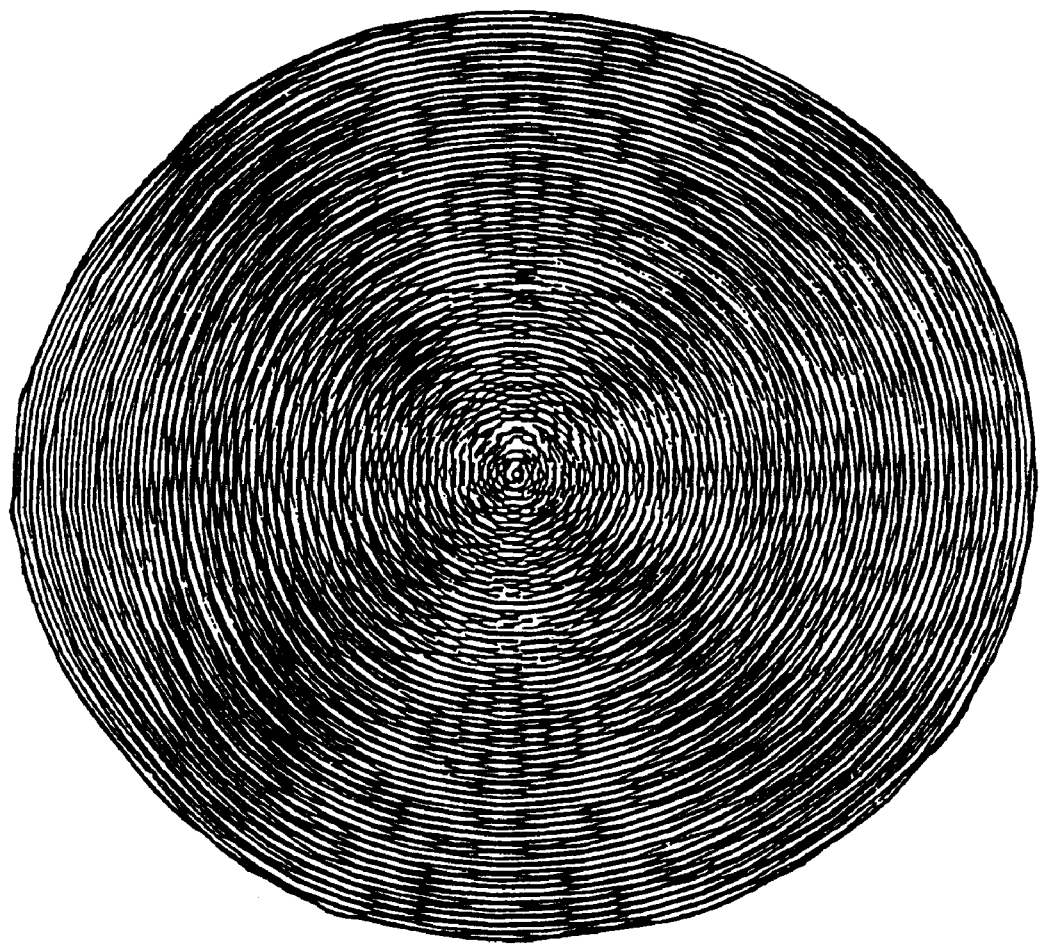
FIG. 15 is a projection on a plane of equally spaced wave fronts for an aircraft engine part.

A set of 60 geodesics are defined as developing from the center of the seal. The calculation of the wave fronts is the locus of all equidistant points along the geodesics. FIG. 12 illustrates a set of geodesics with different directions and the same parameter length along two patches is plotted in two dimensions. The geodesics for a first patch are shown in dashed lines and the geodesics for the adjacent patch are shown in solid lines. This same geodesic set is shown in three dimensions FIG. 13 and superimposed on the two patches in FIG. 14. From the set of geodesics, the loci of equidistant SAW wave fronts is determined as illustrated in FIG. 15. The identification of such loci is a requirement for the SAFT reconstruction.

The present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

The disclosure above is directed to use of the invention with a homogenous and isotropic material. It is understood by those skilled in the art that the invention may also be applied to heterogeneous, anisotropic materials. While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for determining surface acoustic wave paths for an object comprising:

obtaining a representation of the object;

determining from said representation of the object a plurality of geodesics from a point on the object;

determining a plurality of surface acoustic wave ray paths in response to said plurality of geodesics; and determining a plurality of equally spaced surface acoustic wave fronts in response to said surface acoustic wave ray paths.

2. The method of claim 1 wherein:

said determining a plurality of geodesics includes dividing said object into a plurality of patches and determining said geodesics for each of said patches.

3. The method of claim 2 wherein:

said determining said geodesics for each of said patches includes obtaining parametrical expressions for each patch using a non-uniform rational B-spline fitting method.

4. The method of claim 3 wherein:

said determining said geodesics for each of said patches includes determining intrinsic metric elements for each of said patches in response to said parametrical expressions.

5. The method of claim 4 wherein:

said intrinsic metric elements are Christoffel symbols.

6. The method of claim 1 further comprising:

utilizing said plurality of equally spaced surface acoustic wave fronts in a synthetic aperture focusing technique to generate an image of said object.

7. The method of claim 1 further comprising:

utilizing said plurality of equally spaced surface acoustic wave fronts in a synthetic aperture focusing technique to detect a defect in said object.

8. A storage medium encoded with machine-readable computer program code for determining surface acoustic wave paths for an object for causing a computer to implement a method of:

obtaining a representation of the object;

determining from said representation of the object a plurality of geodesics from a point on the object;

determining a plurality of surface acoustic wave ray paths in response to said plurality of geodesics; and determining a plurality of equally spaced surface acoustic wave fronts in response to said surface acoustic wave ray paths.

9. The storage medium of claim 8 wherein:

said determining a plurality of geodesics includes dividing said object into a plurality of patches and determining said geodesics for each of said patches.

10. The storage medium of claim 9 wherein:

said determining said geodesics for each of said patches includes obtaining parametrical expressions for each patch using a non-uniform rational B-spline fitting method.

11. The storage medium of claim 10 wherein:

said determining said geodesics for each of said patches includes determining intrinsic metric elements for each of said patches in response to said parametrical expressions.

12. The storage medium of claim 11 wherein:

said intrinsic metric elements are Christoffel symbols.

13. The storage medium of claim 8 further comprising instructions:

utilizing said plurality of equally spaced surface acoustic wave fronts in a synthetic aperture focusing technique to generate an image of said object.

14. The storage medium of claim 8 further comprising computer program code for causing a computer to utilize said plurality of equally spaced surface acoustic wave fronts in a synthetic aperture focusing technique to generate an image of said object.

15. The storage medium of claim 8 further comprising computer program code for causing a computer to utilize said plurality of equally spaced surface acoustic wave fronts in a synthetic aperture focusing technique to detect a defect in said object.

* * * * *